(12) United States Patent
Gautam

(10) Patent No.: US 10,039,616 B2
(45) Date of Patent: Aug. 7, 2018

(54) ORTHODONTIC BRACKET

(71) Applicant: Pawan Gautam, Las Vegas, NV (US)

(72) Inventor: Pawan Gautam, Las Vegas, NV (US)

(*) Notice: Subject to any disclaimer, the term of this patent is extended or adjusted under 35 U.S.C. 154(b) by 0 days.

(21) Appl. No.: 14/269,108

(22) Filed: May 3, 2014

(65) Prior Publication Data
US 2015/0250561 A1   Sep. 10, 2015

Related U.S. Application Data

(62) Division of application No. 14/202,656, filed on Mar. 10, 2014, now abandoned.

(51) Int. Cl.
*A61C 7/14* (2006.01)
*A61C 7/00* (2006.01)
*A61C 7/28* (2006.01)
*A61C 7/30* (2006.01)
*A61C 7/36* (2006.01)

(52) U.S. Cl.
CPC ............. *A61C 7/002* (2013.01); *A61C 7/14* (2013.01); *A61C 7/28* (2013.01); *A61C 7/287* (2013.01); *A61C 7/30* (2013.01); *A61C 7/36* (2013.01)

(58) Field of Classification Search
CPC ........... A61C 7/00; A61C 7/002; A61C 7/026; A61C 7/12; A61C 7/14; A61C 7/145; A61C 7/146; A61C 7/16; A61C 7/20; A61C 7/28

USPC .......................... 433/8–13, 15, 16, 18–20, 24
See application file for complete search history.

(56) References Cited

U.S. PATENT DOCUMENTS

| | | | | |
|---|---|---|---|---|
| 3,423,833 A | * | 1/1969 | Pearlman | ........................ 433/16 |
| 4,487,581 A | * | 12/1984 | Adler | ...................... A61C 7/30 |
| | | | | 433/16 |
| 2005/0244781 A1 | * | 11/2005 | Abels et al. | .................... 433/24 |
| 2007/0092849 A1 | | 4/2007 | Cosse | |
| 2011/0311935 A1 | * | 12/2011 | Dumas | ............................ 433/16 |
| 2012/0288816 A1 | * | 11/2012 | Dupray | .................. A61C 7/143 |
| | | | | 433/10 |

* cited by examiner

*Primary Examiner* — Ralph Lewis
(74) *Attorney, Agent, or Firm* — Patent Central LLC; Stephan A. Pendorf

(57) ABSTRACT

An orthodontic bracket consisting of two-components that are engaged and locked together to form the bracket assembly where the tooth component of the orthodontic bracket is semi-permanently glued to the tooth surface and the wire component of the orthodontic bracket is securely attached to the wire. When the wire component and the tooth component of the bracket assembly are engaged, the orthodontic wire that passes through the wire component of the bracket is deflected as a result; the alignment of the teeth occurs due to the elastic recoil of the orthodontic wire. The wire component of the bracket is completely detachable and re-attachable to the tooth component of the bracket.

3 Claims, 4 Drawing Sheets

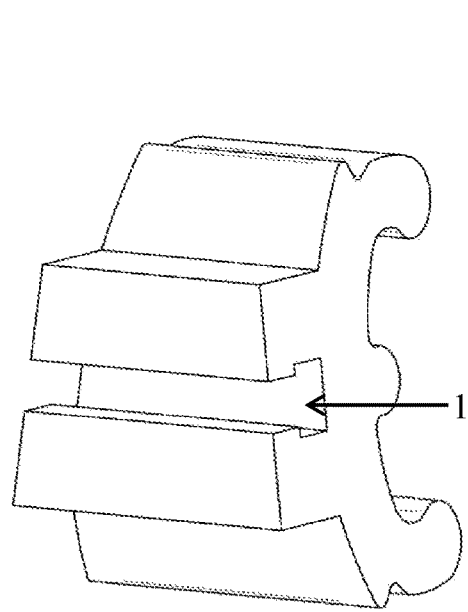
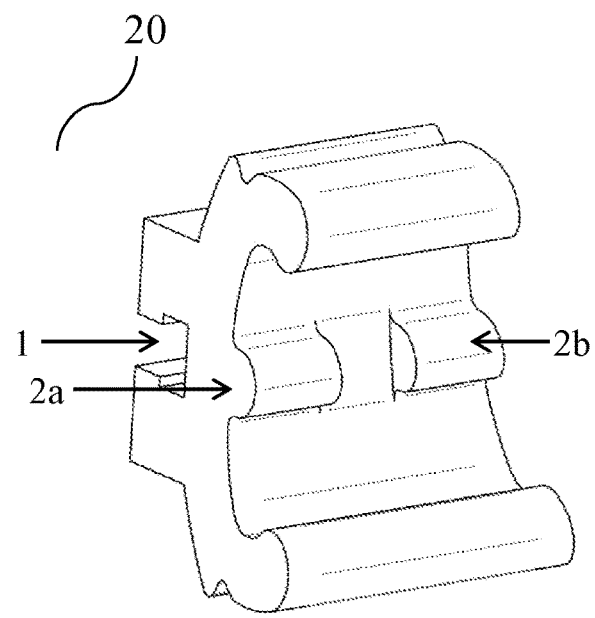
FIG. 1
FIG. 2
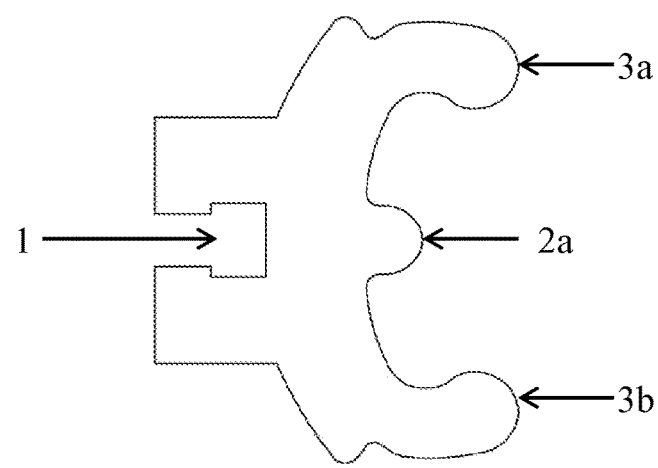
FIG. 3

ORTHODONTIC BRACKET

CROSS REFERENCE TO RELATED APPLICATION

This application is related to U.S. Provisional Patent Application Ser. No. 61/776,436 filed, Mar. 11, 2013 and U.S. Non Provisional patent application entitled "ORTHODONTIC APPLIANCE" application Ser. No. 14/202,656, filed Mar. 10, 2014, which is incorporated herein by reference in its entirety.

FIELD OF THE INVENTION

The present invention is generally related to orthodontic appliances. More particularly, the invention relates to an orthodontic bracket consisting of two components, one that holds the wire (wire component) and the other that is attached to the teeth (tooth component). The wire component locks in with the tooth component affixed to the mal-aligned teeth to form the bracket assembly that results in deflection and recoil of the wire, to bring the mail-aligned teeth into a rapid three dimensional alignment with minimum friction.

BACKGROUND OF THE INVENTION

Mal-aligned teeth detract from the aesthetic appeal of a smile and impart a negative image of the wearer of the smile. Therefore, straightening and aligning mal-aligned teeth has gained in popularity over the years. Correcting mal-aligned teeth is the exclusive domain of orthodontists who use various implements and procedures to align a patient's teeth. The underlying principle in aligning mal-aligned teeth involves forcing movement of the mal-aligned teeth from their designated positions and re-positioning them to align with the rest of the teeth. To accomplish this method of orthodontic tooth movement, orthodontists use different appliances. The most commonly used orthodontic appliance is the edgewise appliance and its variation, namely the straight wire appliance.

The edgewise appliance system uses a combination of many individual pieces designed to function in a coordinated fashion. The two primary components of this system are, 1) tooth attachments in the form of brackets and bands, and 2) arch wires that engage the brackets and bands. These attachments which are semi-permanently and rigidly attached to the teeth serve as a handle by which force generated by the wires may be transmitted to the teeth to accomplish orthodontic tooth movement. Each attachment in this system is comprised of an orthodontic bracket bonded to the teeth with adhesives and having a rectangular slot that is capable of receiving and accommodating an arch wire with a round, rectangular or square cross section. The arch wires are held within the bracket slot using ligature ties and are a removable component of the system. During treatment, the orthodontist removes the arch wire and makes adjustments to the same wire or inserts new wires in the bracket slot. The optimum three dimensional movement of the tooth is accomplished when the rectangular slot of the bracket is completely or nearly completely filled by a rectangular arch wire. Even with the rectangular arch wire completely filling the rectangular slot of the bracket, all three degrees of control or movement of the teeth may not be efficient due to the bracket-wire play which is essentially brought about by the difference in size of the bracket slot and the arch wire engaged in that slot. Typically, elastic deflection of the arch wire generates forces that are transmitted to the teeth by the brackets attached to the teeth, thereby causing the teeth to move to a desired position. The degree of elastic deflection of the arch wire in turn depends on the properties of the material used in the construction of the wire and the size, shape and cross section of the arch wire.

In a straight wire appliance system, the angulations and inclinations of the teeth are built into the bracket eliminating the need for bending the arch wires to accomplish tooth movement. In theory, the brackets are rigidly fixed to the teeth at their precise pre-programmed or pre-adjusted positions on the mid-facial or lingual aspect of the teeth at their respective mal-aligned positions. The straight, flat, wire is then deflected to engage the bracket slots. The force generated by the elastic deformation of the wire then pulls the teeth along with it as it moves to its original shape, thereby aligning the teeth. Due to the inherent structural differences in tooth size and shape, while the general shape of the bracket may be very similar, for each particular tooth type the corresponding bracket is designed with specific compensation in the base shape, base size, general shape, slot angulations, base thickness etc, to accommodate for differences in tooth shape, size and its spatial relation relative to the horizontal plane.

Initial stages of the orthodontic treatment are accomplished using small size round wires. Although a relatively thinner wire having a round cross-section does not allow application of torquing (labio-lingual inclination of tooth) forces when engaged within an arch wire slot, it does provide a greater degree of flexibility and generally applies less force in use, which is more comfortable for the patient. The characteristic low force of round arch wires is due to their thinner cross-section. As such, wires having a round cross-section are often useful during the beginning stages of orthodontic treatment when the teeth are most mal-aligned. Use of a round arch wire allows for movement of teeth to correct mainly angulations and rotation with relatively light and therefore more comfortable forces. In this phase, the wire is loosely held in the bracket slot to allow sliding of the wire with minimal friction so that the brackets and the teeth attached to them are moved into alignment. A form of brackets called self-legating brackets have been claimed to perform better in this phase due to passive ligation and minimal forces exerted on the wire, consequently resulting in low friction. Once these corrections have been achieved, a relatively thicker square or rectangular wire typically replaces the round arch wire so as to allow torquing of selected teeth to accomplish labio-lingual inclination of the teeth. Torquing is the most difficult tooth movement to accomplish due to small moment arm. Torquing requires use of thicker and stiffer rectangular wires that engage the bracket slot completely (to avoid play). The use of such wires generates heavy forces that have been documented to cause undesirable side effects like orthodontic root resorption.

The conventional orthodontic treatment systems thus described are a cumbersome process and the bracket-wire interaction during the treatment lacks complete three dimensional control, especially in the initial stages of orthodontic treatment. The orthodontic bracket of the present invention can facilitate a true three dimensional movement of the teeth, bringing them into alignment during the entire orthodontic treatment period because all movements can occur simultaneously to move the teeth from their initial mal-aligned stage to the final aligned stage thereby shortening the treatment time, as opposed to conventional orthodontic treatments where a three dimensional control is achieved only in the later stages of the treatment. In general, the orthodontic bracket of the present invention addresses many limitations of conventional orthodontic treatments.

SUMMARY OF THE INVENTION

The present invention is a orthodontic bracket that consists of two-components namely, the wire component and the tooth component. The two components of the orthodontic bracket of the present invention can be engaged and locked in to form the bracket assembly. In addition to providing a better three-dimensional control of the tooth movement, such a two component bracket assembly will provide the patient with the flexibility to remove one of the components of the bracket assembly along with wire attached to it and providing the benefit of promoting better oral hygiene and ease of flossing.

In the exemplary embodiment of the present invention, the orthodontic bracket comprises of a wire component and a tooth component, where the orthodontic wire is attached to the wire component to form the bracket assembly. In this embodiment, the tooth component is semi-permanently glued to the teeth surface and the wire component holds the wire. When wire component (along with the wire) and tooth component are engaged, forces are transmitted to move the teeth due to the deflection of the wire and the alignment of the teeth occurs due to the elastic recoil of the wire.

In the preferred embodiment of the present invention, the tooth component and the wire component when engaged have a minimum three point contact or two-surface contact to allow for all desirable movement of the tooth to be generated when the tooth and wire components of the bracket assembly are engaged. Although less desirable, a one or two point contact or one surface contact between the tooth and wire components are also within the scope of the invention.

In the preferred embodiment of the present invention, the incisal or occlusal surfaces and the gingival/apical surface of the wire component engages the corresponding concavity on the tooth component. Other modifications and means of attachment can also be used to engage the wire and tooth components of the bracket assembly.

The two component bracket assembly of the present invention allows moments arms for mesiodistal rotation, labio-lingual inclination and mesio-distal angulations (tip). The use of the orthodontic bracket of the present invention, allows three dimensional alignment of the teeth during all stages of the orthodontic treatment. Effective torsional forces can be applied with small cross section square or rectangular wires due to the mode of attachment of the two components of the bracket assembly thereby increasing the torsional moment on the tooth and the tooth is moved to its intended position with all desirable movements occurring simultaneously, thereby shortening the treatment duration.

In embodiments of the orthodontic bracket of the present invention, tooth movement can be accomplished with low forces including torquing of the tooth without the use of rigid, thicker wires and better three dimensional control can be achieved even with small cross section wires. The increase in the lever arm length allows the appliance to apply more effective torsional force resulting in an increase in the torsional moment.

The orthodontic bracket of the present invention promotes better oral hygiene due to elimination of metal and elastomeric ligature ties that are used to hold the wire in place. The convenience of disengaging and detaching the entire wire component from the tooth component further promotes oral hygiene and facilitates ease of flossing.

The orthodontic bracket of the present invention can be customized to be used on either labial or lingual tooth surface. In yet another embodiment, hooks can be incorporated into the tooth component or wire component of the bracket assembly to engage intra-maxillary and/or inter-maxillary elastics used in the orthodontic treatment.

In yet other embodiments of the present invention, the tooth component and the wire component of the bracket assembly may consist of more than one unit working in a coordinated manner.

In embodiments of the orthodontic bracket of the present invention, the bracket assembly may include, but is not limited to the use of plastic, polymers, ceramic, metals, alloys, or shape memory polymer or similar materials. In addition, the bracket assembly may also be composed of a composite material that is a combination of the above mentioned materials.

In this summary of the invention, and in the specification in general, the various references to, "an exemplary embodiment," "preferred embodiment," "yet other embodiments" and "some embodiments" do not necessarily refer to the same embodiment (s). Rather, these references to the various embodiments mean that a particular feature, structure, or characteristic described in conjunction with an embodiment is included in at least some embodiments, but not necessarily all embodiments of the invention. Although the present invention has thus been described with reference to its exemplary and related embodiments, these embodiments should not be construed as limitations on the scope of the invention. It is to be understood by those skilled in the art, that the invention can be implemented in embodiments other than the ones described in this summary of the invention.

The objects, embodiments and features of the present invention as described in this summary of the invention will be further appreciated and will become obvious to one skilled in the art when viewed in conjunction with the accompanying drawings, detailed description of the invention, and the appended claims.

BRIEF DESCRIPTION OF THE DRAWINGS

FIG. 1 is a perspective view of the back side of the wire component of the bracket assembly in the orthodontic appliance device.

FIG. 2 is a perspective view of the front side of the wire component of the bracket assembly in the orthodontic appliance device.

FIG. 3 is a side view of the wire component of the bracket assembly in orthodontic appliance device.

DETAILED DESCRIPTION OF THE INVENTION

Figures 4, 5:
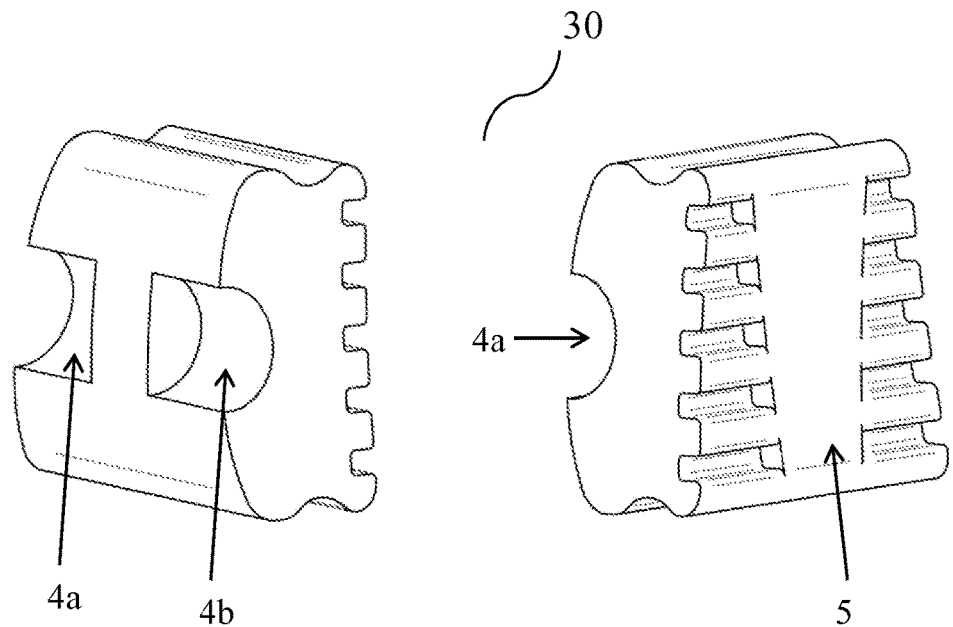
FIG. 4 is a perspective view of the back side of the tooth component of the bracket assembly in the orthodontic appliance device.
FIG. 5 is a perspective view of the front side of the tooth component of the bracket assembly in the orthodontic appliance device.

The appliance of the present invention is an orthodontic bracket consisting of a two-component bracket assembly where one of the components of the bracket assembly, namely the tooth component is semi-permanently glued to the tooth surface and the other component of the bracket assembly, namely the wire component is securely attached to the wire. In the exemplary embodiment of the invention, the orthodontic bracket of the present invention will transmit the forces to move the teeth into alignment when the wire component and the tooth component of the bracket are engaged to form the bracket assembly which results in deflection of the wire and the alignment of the teeth occurs due to the elastic recoil of the wire. The two components of the orthodontic bracket of the present invention are completely detachable and re-attachable. The convenience of disengaging and detaching the wire component from the tooth component of the orthodontic bracket of the present invention further promotes oral hygiene and facilitates ease of flossing.

FIG. 1, FIG. 2 and FIG. 3 show perspective views of the wire attaching bracket component 20 of the orthodontic bracket of the present invention. FIG. 1 is a perspective view of the back side of the wire attaching bracket component 20 showing the wire slot 1 into which the orthodontic wire (not shown here) is inserted. FIG. 2 is the perspective front view of the wire attaching bracket component 20 illustrating the positioning of the lateral wings 2a and 2b which function to prevent the sliding of the wire attaching bracket component 20 on the tooth component. FIG. 2 is a side perspective view of the wire attaching bracket component 20. This view shows the cervical section 3a of the wire attaching bracket component 20 and the occlusal/incisal section 3b of the wire attaching bracket component 20. These sections will fill in the concavities on the tooth component of the orthodontic bracket to form the bracket assembly, as shown in the next figure.

Figure 6:
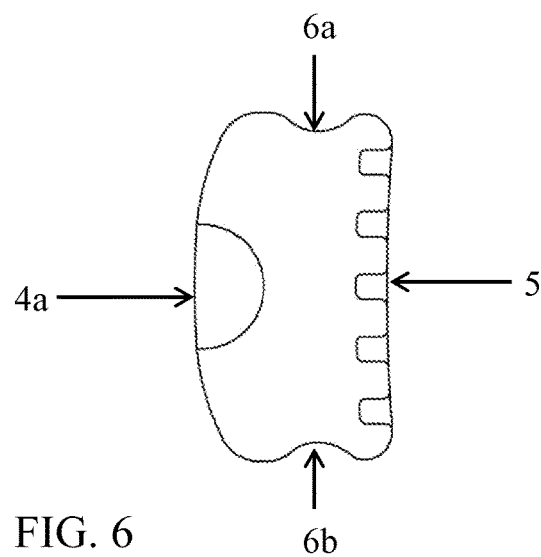
FIG. 6 is a side view of the tooth component of the bracket assembly in the orthodontic appliance device.

FIG. 4, FIG. 5 and FIG. 6 are perspective views of the tooth attaching bracket component 30 of the orthodontic bracket. FIG. 4 is a perspective view of the back side of the tooth attaching bracket component 30 illustrating the slots 4a and 4b for the corresponding lateral wings 2a and 2b of the wire attaching bracket component 20 shown in FIG. 2. FIG. 5 is a perspective view of the front side of the tooth attaching bracket component 30 having a set of mechanical retention grooves 5 that are used to anchor the tooth attaching bracket component 30 to the tooth surface. FIG. 6 is a side view of the tooth attaching bracket component 30 of the orthodontic bracket illustrating the cervical concavity 6a for the cervical section 3a and the occlusal/incisal concavity for the corresponding section 3b of the wire attaching bracket component 20 in FIG. 3.

Figures 7, 8:
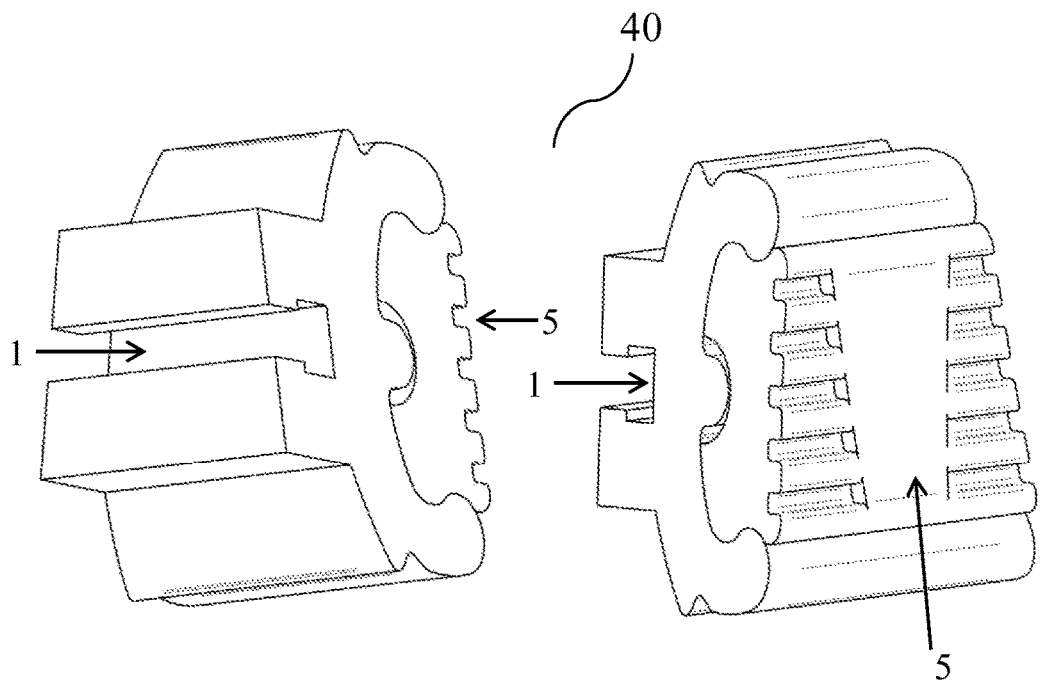
FIG. 7 is a perspective back view of the bracket assembly comprising the tooth and wire components.
FIG. 8 is a perspective front view of the bracket assembly comprising the tooth and wire components.
Figure 9:
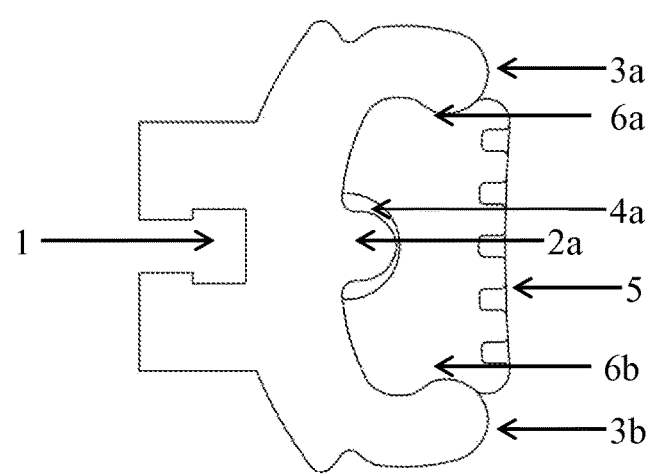
FIG. 9 is a perspective side view of the bracket assembly comprising the tooth and wire components.

FIG. 7, FIG. 8 and FIG. 9 are perspective views of the bracket assembly 40 formed when the wire component and the tooth component interact and are locked in place. FIG. 7 and FIG. 8 show the wire slot 1 of the wire component and the set of mechanical retention grooves 5 of the tooth component facing away from each other when the two components are locked together to form the bracket assembly 40. FIG. 9 is a side perspective view of the bracket assembly 40 illustrating the wire slot 1 and the lateral wing 2a on the wire component locking in to the slot 4a in the tooth component. The sections 3a and 3b on the wire component are also locked into the respective concavity for cervical portion 6a and the occlusal/incisal portion 6b of the tooth component.

Figure 10:
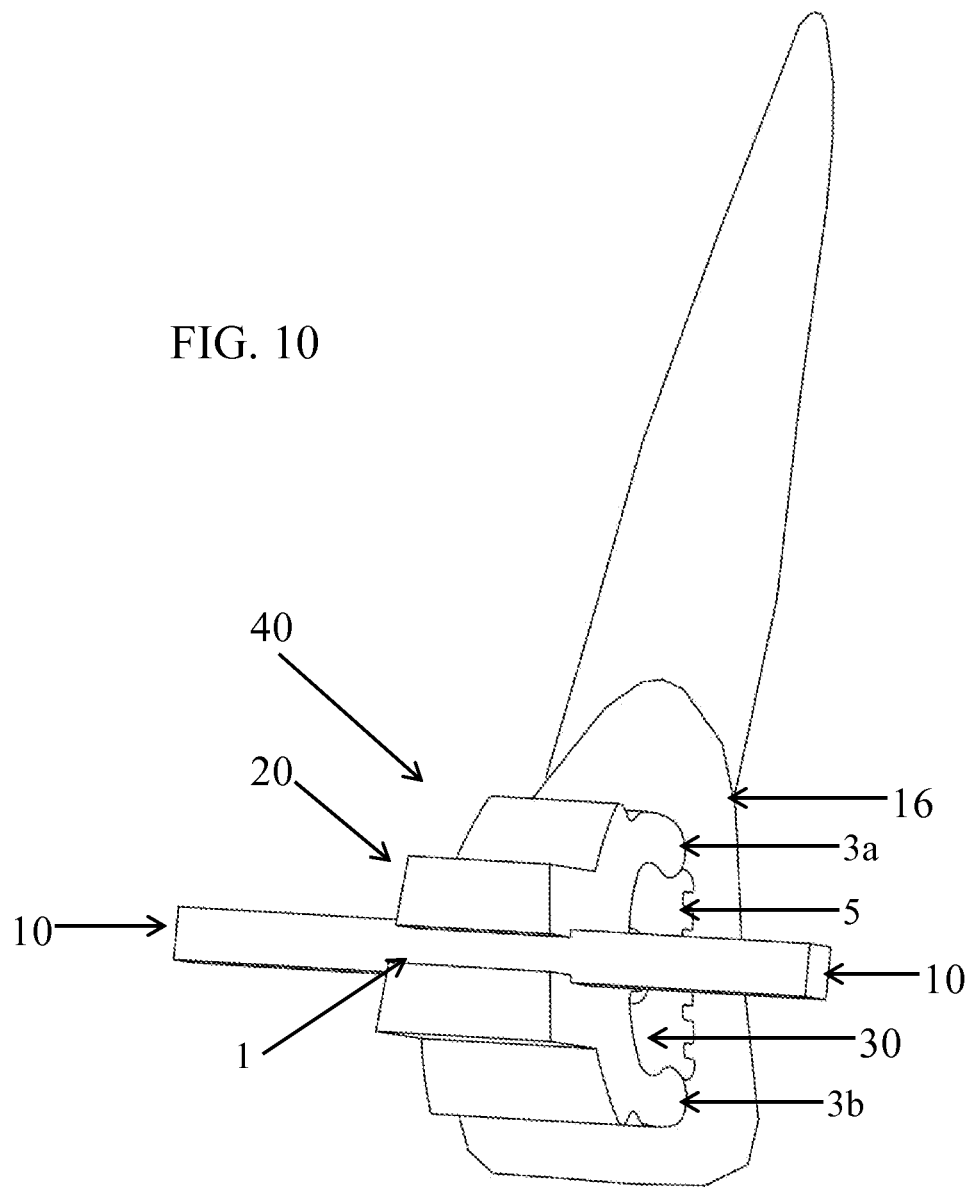
FIG. 10 is a perspective view of the bracket assembly attached to a tooth surface.

FIG. 10 is a perspective view of the bracket assembly 40 attached to the tooth surface 16. The orthodontic wire 10 is enclosed securely within the wire slot 1 of the wire component 20. The wire attaching bracket component 20 is then locked in with the tooth attaching bracket component 30 to form the bracket assembly 40. The mechanical retention grooves, 5 of the tooth attaching bracket component 30 facilitates attachment of the tooth attaching bracket component to the tooth surface 16 which is generally accomplished using adhesives. The wire attaching bracket component 20 when attached to orthodontic wire 10 is at custom orientation and position and constitutes the customized orthodontic appliance for tooth alignment. Once this arrangement of the orthodontic wire 10 within the slot of the wire attaching bracket component 20 is achieved, the orthodontic wire 10 is attached to the wire attaching bracket component 20 of the bracket assembly so that there is limited sliding or no sliding at all back and forth, or rotation of the wire in the wire slot of the wire attaching bracket component 20, preferably by mechanical interlocking, adhesion, or welding.

The foregoing description of the exemplary embodiments of the present invention through the drawings and the detailed description of the manner of using the orthodontic bracket should not be construed to limit the scope of the invention. It is to be understood that the embodiment of the present invention as described herein do not limit any application or scope of the invention and that the invention can be carried out and practiced in various ways and implemented in embodiments other than the one outlined in the description above. It is to be further understood that the phraseology and terminology used to describe the invention are for descriptive purposes only. It should be understood and obvious to one skilled in the art that alternatives, modifications, and variations of the embodiment of the present invention may be construed as being within the spirit and scope of the appended claims.

What is claimed is:

1. An orthodontic appliance for aligning teeth, the orthodontic appliance comprising:
    at least one arch wire,
    a plurality of bracket assemblies adapted for forming an attachment between said arch wire and teeth, each bracket assembly comprising a two-part bracket, each two-part bracket comprising:
        a wire-attaching bracket component, and
        a tooth-attaching bracket component,
    said wire-attaching bracket component having a first side and a second side, said first side having a wire slot, said at least one arch wire received and fixedly attached in said wire slot of each of said wire-attaching bracket components and held rigidly without sliding or rotation by mechanical interlocking, adhesion, or welding to form a wire-and-wire-attaching-bracket-component assembly, said second side having means for releasable mating attachment to said tooth-attaching bracket component,
    said tooth-attaching bracket component having a first side and a second side, said first side having means for releasable mating attachment to said wire-attaching bracket component second side, said tooth-attaching bracket component second side having a tooth-attachment surface being adapted to being adhesively attached to a surface of a tooth, the orthodontic appliance configured to transmit moment arms from the arch wire to the tooth via the bracket assemblies, wherein said means for releasable attachment of said wire-attaching bracket component to said tooth-attaching bracket component prevents movement of the wire-attaching bracket component relative to the tooth-attaching bracket component both (a) perpendicular to the wire slot axis parallel to the attachment surface and (b) parallel to the wire slot axis, wherein the wire-and-wire-attaching-bracket-component assembly is adapted to being separated intact from the plurality of tooth-attaching bracket components by pulling the wire-and-wire-attaching-bracket-component assembly perpendicular to said tooth-attachment surface, without first releasing the wire from the wire-attaching bracket components, and wherein one of the second side of the wire-attaching bracket component and the first side of the tooth-attaching bracket component comprises lateral wings defining a slot between them and first and second clamping elements, and the other of the second side of the wire-attaching bracket component and the first side of the tooth-attaching bracket component comprises recesses having a ridge between them adapted for mating engagement with said lateral wings and having first and second concavities adapted for mating engagement with said clamping elements.

2. An orthodontic appliance as in claim 1, wherein each of said wire slots is configured to receive a polygon shaped cross-section arch wire with three or more sides in a manner that nearly completely or completely fills said slot.

3. The orthodontic appliance as in claim 1, wherein said wire-and-wire-attaching-bracket-component assembly after being separated from the tooth-attaching bracket components by pulling on the wire-and-wire-attaching-bracket-component assembly can be reattached to said tooth-attaching bracket components as said wire-and-wire-attaching-bracket-component assembly.

\* \* \* \* \*